United States Patent [19]

Constantini et al.

[11] Patent Number: 5,160,496
[45] Date of Patent: Nov. 3, 1992

[54] HYDROXYLATION OF PHENOLS/PHENOL ETHERS

[75] Inventors: Michel Constantini, Lyons; Jean-Michel Popa, Drancy, both of France

[73] Assignee: Rhone-Poulenc Chimie, Courbevoie, France

[21] Appl. No.: 552,840

[22] Filed: Jul. 16, 1990

Related U.S. Application Data

[63] Continuation of Ser. No. 220,175, Jul. 18, 1988, abandoned.

[30] Foreign Application Priority Data

Jul. 17, 1987 [FR] France .................. 87 10420

[51] Int. Cl.$^5$ ................................ C07C 37/60
[52] U.S. Cl. ................... 568/771; 568/629; 568/630; 568/803; 568/815
[58] Field of Search ........... 568/771, 803, 815, 629, 568/630

[56] References Cited

U.S. PATENT DOCUMENTS

| 3,514,490 | 5/1970 | Marland | 568/771 |
| 3,589,956 | 5/1971 | Bloch. | |
| 4,578,521 | 5/1986 | Chang et al. | 568/771 |

FOREIGN PATENT DOCUMENTS 163560 12/1985 European Pat. Off. .
2116974 10/1983 United Kingdom .

OTHER PUBLICATIONS

Kirk-Othmer Encyclopedia of Chemical Technology, 3d ed., vol. 15, pp. 654–658 (1981).
McGraw-Hill Encyclopedia of Science & Technology, 6th Edition, vol. 3, pp. 653–661.
McGraw-Hill Encyclopedia of Science & Technology, 6th Edition, vol. 19, pp. 617–618.

Primary Examiner—Jose G. Dees
Assistant Examiner—B. Frazier
Attorney, Agent, or Firm—Burns, Doane, Swecker & Mathis

[57] ABSTRACT

The phenols and phenol ethers are economically and efficiently hydroxylated using hydrogen peroxide, in the presence of a catalytically effective amount of a bridged clay, e.g., a zeolite or smectite.

20 Claims, No Drawings

HYDROXYLATION OF PHENOLS/PHENOL ETHERS

This application is a continuation, of application Ser. No. 07/220,175, filed Jul. 18, 1988, now abandoned.

BACKGROUND OF THE INVENTION

Field of the Invention

The present invention relates to the hydroxylation of phenols or phenol ethers, and, more especially, to the hydroxylation of phenols or phenol ethers using hydrogen peroxide.

Description of the Prior Art

The preparation of diphenols by hydroxylation of phenol or substituted phenols, using hydrogen peroxide, is known to this art.

French Patent No. 69/45,467, published under No. 2,071,464, describes a process in which the reaction is catalyzed by a strong acid such as, for example, perchloric acid or sulfuric acid.

German Patent No. 2,410,742 describes a process similar to the above, in which hydrogen peroxide is employed in the form of a virtually anhydrous organic solution.

These two processes are of considerable interest and the former is utilized industrially.

However, for a number of years attempts have been made to catalyze the hydroxylation reaction using solids which are not dissolved in the medium, in order to simplify their separation from the reaction medium and their recycling if desired, and to avoid the saline by-products which are formed in most cases when the dissolved acidic catalysts are removed.

Thus, French Patent 81/17,023 (published under No. 2,489,816) recommends the use of titanium silicalite as a heterogeneous catalyst for the hydroxylation of aromatic compounds using hydrogen peroxide.

The fine size of the catalyst particles which are employed makes such particulates very difficult to separate from the reaction medium and their recycling questionable, whereas, in an industrial process, it is essential to be able to recycle a costly catalyst.

In order to overcome this problem of catalyst separation, it has been proposed, in published European Patent Application No. 200,260, to employ agglomerates of these fine particles of titanium silicalite.

Nonetheless, a need continues to exist in this art for a heterogeneous catalysis of the hydroxylation reaction of phenols or phenol ethers using hydrogen peroxide, which can be employed industrially under economically acceptable conditions.

Cf. U.S. Pat. No. 3,580,956, FR-A-2,563,446 and GB-A-2,116,974.

SUMMARY OF THE INVENTION

Accordingly, a major object of the present invention is the provision of an improved, economically and technically attractive process for the hydroxylation of phenols or phenol ethers by means of hydrogen peroxide.

Briefly, the present invention features the hydroxylation of phenols or phenol ethers having the general formula (I):

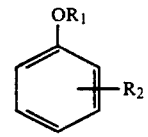

in which:

$R_1$ is a hydrogen atom, a methyl group, an ethyl group or a phenyl group, $R_2$ is a hydrogen atom, an alkyl radical containing 1 to 4 carbon atoms, an alkoxy radical containing 1 to 4 carbon atoms, or a phenyl or cyclohexyl radical, by reacting such phenols or phenol ethers with hydrogen peroxide in the presence of a catalytically effective amount of at least one bridged clay.

DETAILED DESCRIPTION OF THE PREFERRED EMBODIMENTS OF THE INVENTION

More particularly according to the present invention, by the term "bridged clay" are intended clays, between the flakes of which, bridges or pillars exist which maintain a fundamental spacing therebetween. The fundamental spacing is the sum of the thickness of a leaflet of clay and of the interleaf spacing.

The bridged clays employed in the process of the invention typically have a fundamental spacing which is greater than 10 angstroms (1nm).

The bridged clays are, for example, zeolites with a two-dimensional structure which are prepared according to the bridging process described in French Patent No. 84/06,482 (published under number 2,563,446). These zeolites having a two-dimensional structure are produced by a process comprising the following stages:

(a) treating a natural or synthetic clay, in the form of an aqueous suspension, with an aqueous solution containing at least one hydroxide of at least one metal;

(b) removing excess metal hydroxide which has not reacted with the clay, such removal resulting in a zeolite precursor being produced, after drying of the treated clay;

(c) heat-treating the zeolite precursor, such treatment providing a zeolite having a two-dimensional structure.

It is also possible to employ only the stages (a) and (b) above in order to produce a bridged clay suitable for use according to the invention.

The clays which may be subjected to a bridging treatment are, particularly, smectites. Among these smectites, beidellites, in particular synthetic beidellites and montmorillonites, are especially representative, without implying any limitation.

The preparation of synthetic beidellites which will thus be bridged is itself described in the above-mentioned patent application and in the articles to which said patent application refers.

The clay bridging may be carried out with the aid of hydroxides of the following metals: aluminum, nickel, cobalt, vanadium, molybdenum, rhenium, iron, copper, ruthenium, chromium, lanthanum, cerium, titanium, boron, gallium, zirconium, niobium, tantalum and silicon, as well as with mixed hydroxides of these metals.

A beidellite or a montmorillonite bridged using aluminum hydroxide, for example according to the process of Patent Application FR 84/06,482, will be preferably employed as a catalyst in the present process.

The phenols and phenol ethers which are preferably employed in the process of the invention are the compounds of formula (I) in which $R_1$ is a hydrogen atom, a methyl group or an ethyl group, and $R_2$ is a hydrogen atom, a methyl, ethyl or tert-butyl group, or a methoxy or ethoxy group.

Phenol, anisole, ortho-cresol, meta-cresol, para-cresol, 4-tert-butylphenol, 2-methoxyphenol and 4-methoxyphenol are especially representative.

The process of the invention is particularly notably applicable to phenol for the preparation of hydroquinone and of pyrocatechine.

The hydrogen peroxide may be used in the form of an aqueous solution, generally having a hydrogen peroxide concentration higher than 20% by weight. The hydrogen peroxide may also be used in the form of a solution in an organic solvent. Among the organic solvents useful for formulating such solutions of hydrogen peroxide, representative are the esters such as, especially, alkyl or cycloalkyl esters of saturated aliphatic carboxylic acids; alkyl acetates and propionates containing from 4 to 8 total carbon atoms or mixtures of such esters will preferably be employed. It is also possible to employ solutions of hydrogen peroxide in an ether such as, for example, dioxane, diisopropyl ether or methyl tert-butyl ether.

The molar ratio of the phenols or phenol ethers of formula (I) to hydrogen peroxide typically ranges from 25/1 to 3/1 and preferably from 20/1 to 4/1. The amount of bridged clay, and more particularly of zeolite having a two-dimensional structure, defined above, which may be employed in the present process can vary over very wide limits.

When the process is carried out noncontinuously, the catalyst may constitute from 0.1% to 20% by weight relative to the weight of the compound of formula (I). This weight ratio will preferably range from 0.5% to 10%. However, when the process is carried out continuously, for example by reacting a mixture of compound of formula (I) and of hydrogen peroxide solution in a stationary catalyst bed, these ratios of catalyst to compound of formula (I) become meaningless and, at a given instant, there could exist an excess by weight of catalyst in relation to the compound of formula (I).

The hydroxylation reaction of the compound (I) can also be carried out in a solvent for said compound (I), which is preferably miscible or partly miscible with water.

Exemplary of such solvents, representative are: water, alcohols such as methanol, tert-butanol, isopropanol or ethanol, ketones such as acetone or methyl isobutyl ketone, nitriles such as acetonitrile, carboxylic acids such as acetic acid, esters such as propyl acetate, ethers such as methyl tert-butyl ether, polar aprotic solvents such as tetrahydrothiophene dioxide (sulfolane), ethylene carbonate, propylene carbonate, and N-methylpyrrolidone.

A phosphorus compound such as a phosphoric acid, a phosphonic acid or one of the derivatives thereof, may also be added. These compounds generally enable the yields of hydroxylated compound to be improved relative to the hydrogen peroxide converted. From 0 to 10 mol % of phosphorus compound is typically employed, relative to hydrogen peroxide.

The temperature at which the reaction is conducted typically ranges from 45° to 160° C. at atmospheric pressure. It is also possible to operate at higher temperatures and at a pressure above atmospheric pressure.

In order to further illustrate the present invention and the advantages thereof, the following specific examples are given, it being understood that same are intended only as illustrative and in nowise limitative.

EXAMPLE 1

Preparation of Catalyst TRP-1 (according to the process of Patent Application FR 84/06,482):

Beidellite is a TOT clay, a silicoaluminate of the dioctahedral smectite type, in which some of the silicon atoms in the tetrahedral layer are substituted by aluminum atoms.

Bridged beidellite was produced by bridging a sodium-containing beidellite, using an aluminum hydroxide solution.

The solution of aluminum polyoxycations was prepared by adding aqueous ammonia to a solution of aluminum nitrate up to an OH/AL ratio of 1.2 (pH=4). This solution was then heated for 1 hour at 50° C.

A dispersion of the sodium-containing beidellite in water was prepared, and the above solution was added to it. The mixture of the two solutions was vigorously stirred for 1 hour at ambient temperature. The solution thus obtained was dialyzed for four days.

The material was then filtered off, and then dried at 100° C. for two hours. The dried product was then calcined at 350° C.

After calcination at 350° C., the TRP-1 material thus obtained was characterized by a fundamental spacing of 17.6 angstroms (the interlamellar distance being about 7.6 angstroms) of 17.6 angstroms (1.76 nm), by a specific surface area of 420 $m^2/g$ and by a pore volume of 0.43 $cm^3/g$.

The bridged beidellite produced was in the form of small cylinders approximately 1 to 5 millimeters in length and approximately 0.5 to 1 millimeter in diameter.

EXAMPLE 2

The following materials were charged into a 100-$cm^3$ Pyrex glass reactor equipped with a central stirrer, a condenser connected to a gasometer, a controlled heating system and an injection system, after the apparatus had been purged with nitrogen beforehand:

(i) 27.2 g of phenol, (ii) 0.528 g of bridged beidellite prepared in Example 1.

the mixture was heated under stirring to 80° C., and then 6.32 g of a solution of $H_2O_2$ at a concentration of 40% by weight per volume were injected over 1 hour.

The mixture was permitted to react for an additional 1 hour.

After the catalyst had been filtered off, the unconverted $H_2O_2$ was determined by iodometry, and the diphenols by high performance liquid chromatography (HPLC).

The following results were obtained:

(a) degree of $H_2O_2$ conversion (DC): 31.5%

(b) pyrocatechol yield based on $H_2O_2$ converted (CY): 27.5%

(c) yield of hydroquinone based on $H_2O_2$ converted (CY): 12.5%

(d) total yield of diphenols: 40.0%

EXAMPLE 3

A new test was carried out in the apparatus described in Example 2, following the same operating procedure and using the same reactant charges, the mixture being permitted to react for 5 h, 30 min (instead of one hour) upon completion of the $H_2O_2$ addition.

The converted $H_2O_2$ was determined by iodometry, and the diphenols formed by HPLC.

The following results were obtained:
(a) degree of $H_2O_2$ conversion (DC): 100.0%
(b) yield of pyrocatechol based on $H_2O_2$ converted (CY): 10.0%
(c) yield of hydroquinone based on $H_2O_2$ converted (CY): 8.5%
(d) total yield of diphenols: 18.5%

EXAMPLE 4

Example 2 was repeated, 2 g of the catalyst prepared in Example 1 being charged.

The following results were obtained:
(a) degree of $H_2O_2$ conversion (DC): 81.0%
(b) yield of pyrocatechol based on $H_2O_2$ converted (CY): 8.0%
(c) yield of hydroquinone based on $H_2O_2$ converted (CY): 5.0%
(d) total yield of diphenols: 13.0%

EXAMPLE 5

Example 2 was repeated with the following differences:
(i) 2 g of catalyst of Example 1,
(ii) 1.45 g of aqueous solution of $H_2O_2$ at a concentration of 40% by weight per volume (w/v),
(iii) stirring for 1 h, 30 min, upon completion of $H_2O_2$ addition.

The following results were obtained:
(a) degree of $H_2O_2$ conversion (DC): 97.5%
(b) yield of pyrocatechol based on $H_2O_2$ converted (CY): 9.0%
(c) yield of hydroquinone based on $H_2O_2$ converted (CY): 8.0%
(d) total yield of diphenols: 17.0%

EXAMPLE 6

The following materials were charged into a 30-cm$^3$ Pyrex glass reactor equipped with a magnetic stirrer, a condenser connected to a gasometer, a controlled heating system and an injection system, after the apparatus had first been purged with nitrogen:
(i) 9.4 g of phenol,
(ii) 0.25 g of bridged beidellite prepared in Example 1.

The mixture was heated under stirring to 80° C., and 0.25 g of a solution of $H_2O_2$ containing 70% by weight per volume (5 mmol) was then injected over 0.1 min.

The mixture was permitted to react for an additional 2 h, 30 min.

After the catalyst had been filtered off, the unconverted $H_2O_2$ was determined by iodometry and the diphenols by high performance liquid chromatography (HPLC).

The following results were obtained:
(a) degree of $H_2O_2$ conversion (DC): 71.2%
(b) yield of pyrocatechol based on $H_2O_2$ converted (CY): 12.9%
(c) yield of hydroquinone based on $H_2O_2$ converted (CY): 5.9%
(d) total yield of diphenols: 18.8%

EXAMPLE 7

Example 6 was repeated with the following difference:
0.5 g of the catalyst of Example 1.

The following results were obtained:
(a) degree of $H_2O_2$ conversion (DC): 61.6%
(b) yield of pyrocatechol based on $H_2O_2$ converted (CY): 16.4%
(c) yield of hydroquinone based on $H_2O_2$converted (CY): 8.9%
(d) total yield of diphenols: 25.3%

EXAMPLES 8 TO 15:

The following materials were charged into a 30-cm$^3$ Pyrex glass reactor equipped with a magnetic stirrer, a condenser connected to a gasometer, a controlled heating system and an injection system, after the apparatus had first been purged with nitrogen:
(i) 4.7 g of phenol,
(ii) 0.25 g of bridged beidellite prepared in Example 1,
(iii) 4.7 g of an organic solvent (see Table below).

The mixture was heated under stirring to 80° C. and 0.125 g of a solution of $H_2O_2$ at a concentration of 70% by weight per volume (2.5 mmol) was then injected over 0.1 min.

The mixture was then permitted to react for another 2 h, 30 min.

After the catalyst had been filtered off, the unconverted $H_2O_2$ was determined by iodometry and the diphenols by high performance liquid chromatography (HPLC).

The results obtained are reported in Table I below (pyrocatechol=PC; hydroquinone=HQ).

TABLE I

| EXAMPLES | SOLVENTS | $H_2O_2$ DC % | HQ CY % | PC CY % | Total CY % |
|---|---|---|---|---|---|
| Ex. 8 | acetic acid | 96.1 | 6.5 | 1.9 | 8.4 |
| Ex. 9 | acetonitrile | 17.8 | 4.8 | 11.5 | 16.3 |
| Ex. 10 | methyl isobutyl ketone | 22.3 | 62.3 | 33.4 | 95.7 |
| Ex. 11 | propyl acetate | 18.9 | 5.9 | 10.1 | 16.0 |
| Ex. 12 | tert-butanol | 8.8 | 2.0 | 3.7 | 5.7 |
| Ex. 13 | methanol | 6.2 | 12.1 | 4.6 | 16.7 |
| Ex. 14 | sulpholane | 26.4 | 11.3 | 13.0 | 24.3 |
| Ex. 15 | water | 6.6 | 0 | 7.1 | 7.1 |

EXAMPLES 16 to 18

The following materials were charged into a 30-cm$^3$ Pyrex glass reactor equipped with a magnetic stirrer, a condenser connected to a gasometer, a controlled heating system and an injection system, after the apparatus had first been purged with nitrogen:
(i) 9.4 g of phenol,
(ii) 0.25 g of TRP-1 bridged beidellite prepared in Example 1 (which optionally had been subjected to an additional treatment).

The mixture was heated under stirring to 80° C. or to 130° C., and 0.25 g of a solution of $H_2O_2$ at a concentration of 70% by weight per volume (5 mmol) was then injected over 0.1 min.

The mixture was then permitted to react for another 2 h, 30 min.

After the catalyst had been filtered off, the unconverted $H_2O_2$ was determined by iodometry and the diphenols by high performance liquid chromatography (HPLC).

The results obtained are reported in Table II below (pyrocatechol=PC; hydroquinone=HQ).

TABLE II

| Examples | Additional catalyst treatment | T °C. | $H_2O_2$ DC % | HQ CY % | PC CY % | Total diphenols CY % |
|---|---|---|---|---|---|---|
| Ex. 16 | calcined 5 h at 550° C. | 80 | 50.0 | 11.0 | 23.0 | 34.0 |
| Ex. 17* | none | 80 | 34.5 | 12.5 | 16.5 | 29.0 |
| Ex. 18 | none | 130 | 79.5 | 14.0 | 24.0 | 38.0 |

*test performed in the presence of 4 mol % of 1,1-diphosphonoethanol (DPE) relative to $H_2O_2$

EXAMPLE 19

Examples of bridging of a montmorillonite:

A Wyoming montmorillonite, also known as Volclay bentonite, was employed for these bridging tests.

Preparation of the 2 μm clay fraction

An aqueous suspension containing 20 g/liter of this clay was prepared, was stirred violently and was permitted to settle for 24 hours.

A sample of the 2 μm fraction of the clay was then taken (solution a).

Preparation of clay in sodium form

An excess of sodium chloride, relative to the exchange capacity of the clay, namely, approximately 1,000 milliequivalents of sodium per 100 g of clay, was added to solution a. The solution was stirred for 1 hour at ambient temperature. The clay was then filtered off from the solution. The operation was begun a second time. The clay was then washed with distilled water until chloride ions disappeared from the washings. The clay was then resuspended in water in a proportion of 20 g/liter (solution b).

Preparation of the aluminum hydroxide solution

A 0.4 M aluminum nitrate solution was prepared, and a 0.24 M solution of aqueous ammonia was then added to it slowly and steadily under stirring and at ambient temperature. The pH of the solution was monitored until an OH/Al ratio of 1.2 was obtained. The addition of aqueous ammonia was then stopped. The solution was heated under stirring to 50° C., for approximately 1 hour (solution c).

Bridging state 1.4 liters of solution c were added to 0.9 liter of solution b. The mixture was stirred at ambient temperature for 1 hour. Solution d was obtained.

EXAMPLE 19 A

KMO 15 A and KMO 19 SA

The solution d obtained above was dialyzed with a cellulose acetate dialysis membrane for 4 days against 10 liters of demineralized water, changed daily. The bridged clay was then isolated from the solution by centrifuging.

It was dried for 24 hours at 100° C. and was then calcined for 2 hours at 350° C.

| Interlamellar distance: | KMO 15 A = 17.6 angstroms (1.76 nm) |
| | KMO 19 SA = 18.0 angstroms (1.80 nm) |
| BET specific surface area | KMO 15 A = 240 m$^2$/g |
| | KMO 19 SA = 275 m$^2$/g |
| Pore volume: | KMO 15 A = 0.20 cm$^3$/g |
| | KMO 19 SA = 0.20 cm$^3$/g |

EXAMPLE 19 B

KMO 16 SA:

The bridged clay was isolated from solution d by centrifuging. The centrifugate was introduced into a 2-liter round flask. The volume of demineralized water required to obtain a solution containing 15 g/liter of clay was added. The solution thus obtained was heated to 50° C. for 45 minutes, under stirring at 200 revolutions/minute. It was then allowed to cool. The bridged clay was then isolated from the solution by centrifuging.

It was dried for 24 hours at 100° C. and then calcined for 2 hours at 350° C.

Interlamellar distance: KMO 16 SA = 18.2 angstroms (1.82 nm) BET specific surface

| area: | KMO 16 SA = 130$^2$/g |
| Pore volume: | KMO 16 SA = 0.12 cm$^3$/g |

EXAMPLE 19 C

KMO 20 SA

The bridged clay was isolated from solution d by centrifuging. 2 successive washings of the clay were then carried out at ambient temperature, as follows: the centrifugate was suspended in a volume of demineralized water, such as to provide a solution containing 15 g/liter of clay. Stirring was continued for 1 hour. The clay was isolated by centrifuging and the operation was begun again.

The bridged clay was then centrifuged.

It was dried for 24 hours at 100° C., and then calcined for 2 hours at 350° C.

Interlamellar distance: KMO 20 SA = 18.4 angstroms (1.84 nm) BET specific surface

| area: | KMO 20 SA = 220 m$^2$/g |
| Pore volume: | KMO 20 SA = 0.17 cm$^3$/g |

The various batches of bridged clay prepared in this manner were in powder form.

EXAMPLE 20

Example of bridging of a montmorillonite

A Wyoming montmorillonite, also known as Volclay bentonite, was employed for these tests.

Preparation of the 2 μm clay fraction

An aqueous suspension containing 20 g/liter of this clay was prepared, was stirred violently, and was permitted to settle for 24 hours.

A sample of the 2 μm fraction of the clay was then taken (solution a).

Preparation of the clay in sodium form

An excess of sodium chloride relative to the exchange capacity of the clay, namely, approximately 1,000 milliequivalents of sodium per 100 g of clay, was added to solution a. The solution was stirred for 1 hour at ambient temperature. The clay was then filtered off from the solution. The operation was begun a second time. The clay was then washed with distilled water until chloride ions disappeared from the washings. The clay was then resuspended in water at a concentration of 20 g/liter (solution b).

Preparation of the solution of clay and of aluminum salt

A 0.4 M solution of aluminum nitrate was prepared. 0.5 liter of this solution of aluminum nitrate was added under stirring and at ambient temperature to 1 liter of solution b. Stirring was continued for a few minutes at ambient temperature. Solution c was obtained.

Neutralization of solution c

A 0.5 M solution of aqueous ammonia was added slowly and steadily, under stirring and at ambient temperature, to solution c. The pH of the solution was monitored until an OH/Al ratio of 5 was obtained. The addition of ammonia solution was then stopped. Stirring was continued for approximately 1 hour while the solution was gently warmed.

Isolation of the clay

The solution obtained in the preceding stage was dialyzed with a cellulose acetate dialysis membrane for 4 days against 10 liters of demineralized water which was changed every day. The bridged clay was then isolated from the solution by centrifuging.

It was dried at 100° C. for 24 hours.

Interlamellar distance: KMO 25 II = 14.6 angstroms (1.46 nm).

The bridged clay prepared in this manner was in powder form.

EXAMPLES 21 TO 26

The following materials were charged into a 30-cm$^3$ Pyrex glass reactor equipped with a magnetic stirrer, a condenser connected to a gasometer, a controlled heating system and an injection system, after the apparatus had first been purged with nitrogen:
(i) 4.7 g of phenol (0.05 mol),
(ii) 0.25 g of bridged clay prepared in one of Examples 1, 19 or 20,
(iii) 4.7 g of a solvent (see Table below),
(iv) optionally, 0.1 mmol of 1,1-diphosphonoethanol (DPE) (4 mol % based on $H_2O_2$).

The mixture was heated under stirring to 80° C. or 100° C., and 0.125 g of a solution of $H_2O_2$ at a concentration of 70% by weight per volume (2.5 mmol) was then injected over 0.1 min.

The mixture was then permitted to react for another 2 h, 30 min, or 7 hours.

After the catalyst had been filtered off, the unconverted $H_2O_2$ was determined by iodometry and the diphenols by high performance liquid chromatography (HPLC).

The results obtained are reported in Table III below (pyrocatechol = PC; hydroquinone = HQ).

TABLE III

| Examples | Bridged clay | Solvent | Time | DPE | T °C. | $H_2O_2$ TC % | HQ CY % | PC CY % | Total diphenols CY % |
|---|---|---|---|---|---|---|---|---|---|
| Ex. 21 | TRP-1 | MIBC* | 7 h | yes | 80 | 91.5 | 20.0 | 25.5 | 45.5 |
| Ex. 22 | KMO 20SA | water | 2 h, 30 min | no | 80 | 94.0 | 13.0 | 14.5 | 27.5 |
| Ex. 23 | KMO 19SA | $CH_3CN$ | 2 h, 30 min | no | 80 | 43.5 | 8.0 | 20.5 | 28.5 |
| Ex. 24 | KMO 19SA | sulpholane | 2 h, 30 min | no | 80 | 89.0 | 9.0 | 15.0 | 24.0 |
| Ex. 25 | KMO 25 II | water | 2 hr, 30 min | no | 100 | 95.0 | 19.5 | 23.5 | 43.0 |
| Ex. 26 | KMO 25 II | water | 2 hr, 30 min | yes | 100 | 97.5 | 21.0 | 25.5 | 46.5 |

*MIBC = methyl isobutyl ketone

EXAMPLES 27 to 32

The following materials were charged into a 30-cm$^3$ Pyrex glass reactor equipped with a magnetic stirrer, a condenser connected to a gasometer, a controlled heating system and an injection system, after the apparatus had first been purged with nitrogen:
(i) 9.4 g of phenol (0.1 mol),
(ii) 0.25 g of bridged clay prepared in one of Examples 19 or 20,
(iii) optionally, 0.1 mmol of 1,1diphosphonoethanol (DPE) (4 mol % based on $H_2O_2$).

The mixture was heated under stirring to 80° C., and 0.25 g of a solution of $H_2O_2$ at a concentration of 70% by weight per volume (5 mmol) was then injected over 0.1 min.

The mixture was then permitted to react for another 2 h, 30 min.

After the catalyst had been filtered off, the unconverted $H_2O_2$ was determined by iodometry and the diphenols by high performance liquid chromatography (HPLC).

The results obtained are reported in Table IV below (pyrocatechol = PC; hydroquinone = HQ).

TABLE IV

| Examples | Bridged clay | DPE | $H_2O_2$ DC % | HQ CY % | PC CY % | Total diphenols CY % |
|---|---|---|---|---|---|---|
| Ex. 27 | KMO 15 A | no | 80.0 | 10.0 | 26.0 | 36.0 |
| Ex. 28 | KMO 16 SA | no | 74.0 | 10.5 | 30.0 | 40.5 |
| Ex. 29 | KMO 19 SA | no | 89.5 | 13.0 | 25.5 | 38.5 |
| Ex. 30 | KMO 20 SA | no | 86.5 | 13.5 | 28.0 | 41.5 |
| Ex. 31 | KMO 25 II | no | 88.0 | 12.0 | 28.5 | 40.5 |
| Ex. 32 | KMO 25 II | yes | 48.5 | 21.5 | 39.0 | 60.5 |

EXAMPLES 33

The following materials were charged into a 100-cm$^3$ Pyrex glass reactor equipped with a central stirrer, a condenser connected to a gasometer, a controlled heating system and an injection system after the apparatus had first been purged with nitrogen:
(i) 36.0 g of phenol,
(ii) 0.95 g of bridged clay prepared in Example 20 and calcined at 550° C. for 5 hours : KMO 25 IIA, which had the following characteristics:

| Interlamellar distance: | = 14.3 angstroms (1.43 nm) |
|---|---|
| BET specific surface area: | = 116 m$^2$/g |
| pore volume: | = 0.14 cm$^3$/g, |

(iii) 0.0840 g of 90% $H_3O_{04}$.

The mixture was heated under stirring to 80° C., and then 0.9155 g of a solution of $H_2O_2$ at a concentration of 70% by weight per volume was injected over 3 minutes.

The mixture was then permitted to react for another 5 hours, 30 minutes.

After the catalyst had been filtered off, the unconverted $H_2O_2$ was determined by iodometry and the diphenols by high performance liquid chromatography (HPLC).

The following results were obtained:
(a) degree of conversion (DC) of $H_2O_2$: 91.5%
(b) yield of pyrocatechol based on $H_2O_2$ converted (CY): 31.0%
(c) yield of hydroquinone based on $H_2O_2$ converted (CY): 22.5%
(d) total yield of diphenols: 53.5%

EXAMPLE 34

Example 19A of preparation of bridged clays KMO 15A and KMO 19SA was repeated, but using not only the 2-μm clay fraction (solution a), but the entire suspension.

The characteristics of the bridged clay AAY-2 prepared in this manner were as follows:

| | |
|---|---|
| Interlamellar distance: | 17.6 angstroms (1.76 nm) |
| BET specific surface area: | 220 m²/g |
| pore volume: | 0.2 cm³/g. |

EXAMPLE 35

The following materials were charged into a 100-cm³ Pyrex glass reactor equipped with a central stirrer, a condenser connected to a gasometer, a controlled heating system and an injection system, after the apparatus had first been purged with nitrogen:
(i) 36.0 g of phenol,
(ii) 0.95 g of bridged clay prepared in Example 34: AAY-2.

The mixture was heated under stirring to 80° C., and 0.9155 g of a solution of $H_2O_2$ at a concentration of 70% by weight per volume was then injected over 3 minutes.

The mixture was then permitted to react for another 5 hours, 30 minutes.

After the catalyst had been filtered off, the unconverted $H_2O_2$ was determined by iodometry and the diphenols by high performance liquid chromatography (HPLC).

The following results were obtained:
(a) degree of conversion (DC) of $H_2O_2$: 94.0%
(b) yield of pyrocatechol based on $H_2O_2$ converted (CY): 18.0%
(c) yield of hydroquinone based on $H_2O_2$ converted (CY): 10.5%
(d) total yield of diphenols: 28.5%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxylation of a phenol or phenol ether having the general formula (I):

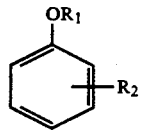

(I)

in which $R_1$ is a hydrogen atom, a methyl group, an ethyl group or a phenyl group, and $R_2$ is a hydrogen atom, an alkyl radical containing 1 to 4 carbon atoms, an alkoxy radical containing 1 to 4 carbon atoms, or a phenyl or cyclohexyl radical, comprising conducting said hydroxylation with hydrogen peroxide, in the presence of a catalytically effective amount of at least one bridged clay.

2. The process as defined by claim 1, said bridged clay having a fundamental spacing greater than 10 angstroms.

3. The process as defined by claim 1, said bridged clay comprising a bridged two-dimensional zeolite.

4. The process as defined by claim 1, said bridged clay comprising a bridged smectite.

5. The process as defined by claim 1, said bridged clay comprising a bridged beidellite.

6. The process as defined by claim 1, said bridged clay comprising a bridged montmorillonite.

7. The process as defined by claim 3, said bridged zeolite having been prepared by (a) treating an aqueous suspension of a natural or synthetic clay, comprising substitutions in a tetrahedral layer, with an aqueous solution of at least one hydroxide of at least one metal, and (b) removing unreacted metal hydroxide therefrom and drying the resulting zeolite precursor.

8. The process as defined by claim 7, said bridged zeolite having been prepared by also (c) heat-treating said zeolite precursor.

9. The process as defined by claim 1, said bridged clay having been prepared by treating a clay with aluminum, nickel, cobalt, vanadium, molybdenum, rhenium, iron, copper, ruthenium, chromium, lanthanum, cerium, titanium, boron, gallium, zirconium, niobium, tantalum or silicon, or with one of the mixed hydroxides thereof.

10. The process as defined by claim 9, said hydroxide comprising aluminum hydroxide.

11. The process as defined by claim 1, wherein said phenol or phenol ether having the general formula (I), $R_1$ is a hydrogen atom, a methyl group or an ethyl group, and $R_2$ is a hydrogen atom, a methyl, ethyl or tert-butyl group or a methoxy or ethoxy group.

12. The process as defined by claim 1, said phenol or phenol ether having the general formula (I) comprising phenol, anisole, ortho-cresol, meta-cresol, para-cresol, 4-tert-butylphenol, 2-methoxyphenol or 4-methoxyphenol.

13. The process as defined by claim 1, wherein the molar ratio of the compound of formula (I) to hydrogen peroxide ranges from 25/1 to 3/1.

14. The process as defined by claim 1, carried out noncontinuously and said bridged clay catalyst constituting from 0.1% to 20% by weight relative to the weight of the compound of formula (I).

15. The process as defined by claim 1, carried out continuously on a stationary catalyst bed.

16. The process as defined by claim 1, wherein the hydrogen peroxide comprises an aqueous solution thereof.

17. The process as defined by claim 1, wherein the hydrogen peroxide comprises an organic solution thereof.

18. The process as defined by claim 1, carried out in a solvent for the compound of formula (I) which is either miscible or partly miscible with water.

19. The process as defined by claim 1, carried out in the presence of 0 to 10 mol % of a phosphoric acid, a phosphonic acid, or derivative thereof, relative to hydrogen peroxide.

20. The process as defined by claim 1, carried out at a temperature of from 45° C. to 160° C.

* * * * *